United States Patent [19]
Psaros

[11] Patent Number: 6,152,132
[45] Date of Patent: Nov. 28, 2000

[54] INSPIRATORY TUBE FOR A VENTILATOR

[75] Inventor: Georgios Psaros, Tullinge, Sweden

[73] Assignee: Siemens Elema AB, Sunndyberg, Sweden

[21] Appl. No.: 09/139,123

[22] Filed: Aug. 25, 1998

[30] Foreign Application Priority Data

Sep. 11, 1997 [SE] Sweden .................................. 9703291

[51] Int. Cl.[7] .............................. A61M 16/00; A62B 7/00; A62B 9/00
[52] U.S. Cl. .............................. 128/204.25; 128/200.24; 128/207.14; 128/971
[58] Field of Search .......................... 128/200.24, 204.18, 128/204.22, 204.23, 204.25, 207.14, 207.15, 911; 604/527

[56] References Cited

U.S. PATENT DOCUMENTS

| | | | |
|---|---|---|---|
| 2,936,761 | 5/1960 | Snyder ..................................... | 604/527 |
| 4,270,530 | 6/1981 | Baum et al. ........................ | 128/204.25 |
| 4,565,194 | 1/1986 | Weerda et al. ..................... | 128/204.23 |
| 4,584,998 | 4/1986 | McGrail ............... | 128/207.15 |
| 4,850,371 | 7/1989 | Broadhurst et al. ..................... | 600/529 |
| 4,966,141 | 10/1990 | Bacaner et al. ..................... | 128/207.14 |
| 4,967,744 | 11/1990 | Chua .................. | 128/204.18 |
| 4,976,261 | 12/1990 | Gluck et al. ....................... | 128/207.15 |
| 5,043,576 | 8/1991 | Broadhurst et al. .................... | 250/293 |
| 5,291,882 | 3/1994 | Makhoul et al. ................... | 128/207.14 |
| 5,372,131 | 12/1994 | Heinen, Jr. ......................... | 128/207.15 |
| 5,379,650 | 1/1995 | Kofoed et al. ....................... | 73/861.52 |
| 5,499,625 | 3/1996 | Frass et al. ......................... | 128/207.15 |
| 5,535,633 | 7/1996 | Kofoed et al. ...................... | 73/861.052 |
| 5,544,648 | 8/1996 | Fischer, Jr. ....................... | 128/207.14 |
| 5,546,935 | 8/1996 | Champeau ......................... | 128/205.23 |
| 5,660,175 | 8/1997 | Daual ................................... | 128/207.15 |
| 5,722,391 | 3/1998 | Rosenkoetter et al. ............ | 128/200.24 |
| 5,765,558 | 6/1998 | Psaros et al. ....................... | 128/207.14 |
| 5,823,184 | 10/1998 | Gross .................................. | 128/294.18 |
| 5,894,839 | 4/1999 | Rosenkoetter et al. ............ | 128/200.24 |
| 5,921,238 | 7/1999 | Bourdon ............................. | 128/204.23 |
| 5,937,855 | 8/1999 | Zdrojkowski et al. ............ | 128/205.24 |
| 5,988,164 | 11/1999 | Paluch ................................. | 128/203.26 |

*Primary Examiner*—John G. Weiss
*Assistant Examiner*—Joseph F. Weiss
*Attorney, Agent, or Firm*—Hill & Simpson

[57] ABSTRACT

An inspiratory tube intended to serve as at least part of an inspiratory line in a ventilator, has a tube wall, a distal end, a proximal end, a gas flow channel for carrying a flow of breathing gas and an opening in the wall at a specific distance from one end of the inspiratory tube, this opening being adapted for connection to an expiratory device (40). The inspiratory tube has a constriction in the gas flow channel between distal end of the inspiratory tube and the opening, a first channel that proceeds within the tube wall, generally parallel to the gas flow channel, and which opens into the gas flow channel between the distal end of the inspiratory tube and the constriction, and a second channel that proceeds within the wall, generally parallel to the gas flow channel, which opens into the gas flow channel between the constriction and the opening. The channels can be connected to a pressure gauge for determining the rate of flow and pressure of gas flowing in the gas flow channel.

7 Claims, 2 Drawing Sheets

INSPIRATORY TUBE FOR A VENTILATOR

BACKGROUND OF THE INVENTION

1. Field of the Invention

The present invention is directed to an inspiratory tube intended for use as at least a part of an overall inspiratory line in a ventilator, the inspiratory tube being of the type having a tube wall, distal and proximal ends, a gas flow channel for carrying a flow of breathing gas, and an opening in the wall at a distance from the distal end of the tube, the opening being adapted for connection of an expiratory device thereto.

2. Description of the Prior Art

An inspiratory tube of the above type is described in PCT Application WO 94/06499. This known ventilator has an inspiratory tube connected to a gas source at one end and to the patient at the other end. An expiratory valve is connected to the inspiratory tube at a specific distance from the patient. In one embodiment, the expiratory valve is connected to a second gas source for the purpose of maintaining a pre-adjustable Positive End-Expiratory Pressure (PEEP). In another embodiment, the expiratory valve is instead connected to the gas source via a valve system in order to maintain PEEP. A pressure gauge and flow meter are arranged in the inspiratory tube between the gas source and the expiratory valve. A control unit controls the entice ventilator. This known ventilator is primarily intended for use as a home care ventilator, i.e. a respirator a patient can use at home.

Interest in home care ventilators is steadily increasing. This is because such a device is advantageous to the patient, who is able to be in her/his own home and can enjoy a greater degree of mobility. There are also public health benefits, since home care frees hospital resources by reducing in-patient treatment time, beds in intensive care being particularly costly. This type of ventilator can be battery-powered and is sometimes referred to as a 'portable' ventilator. Despite this terminology, such a ventilator usually weighs quite a few kilograms and can only be carried around with some difficulty, even by healthy people.

A genuinely portable ventilator, i.e. a ventilator (weighing up to 1 kg, preferably less than 500 g) the patient is easily able to carry, with a capacity sufficient to provide respiratory assistance for several hours, would be even more desirable for patients. Miniaturizing a ventilator to this extent, employing modern turbine, battery and microprocessor technology etc., is thoroughly feasible. One important factor in this process would be to retain every essential function available in a conventional ventilator, such as the ability to maintain a PEEP, to as large an extent as possible. Such a fully portable ventilator would be suitable for virtually every kind of patient. It even could be used as an emergency ventilator for a number of applications and could be included in the basic equipment of e.g. aircraft, buses, boats, ambulances, fire engines, etc.

The known inspiratory tube described above has limitations, since a number of connectors are needed for the pressure gauge and flow meter. This known inspiratory tube also has a design that limits its usefulness and makes the use of separate gas sources or special valve systems necessary for controlling the expiratory valve etc. connected to the inspiratory line.

SUMMARY OF THE INVENTION

An object of the present invention is to provide an inspiratory tube that can be used in a simple and safe fashion for a number of functions with no need for special, additional tubing.

Another object of the invention is to provide an inspiratory tube that is primarily suitable for miniaturization for achieving a fully portable ventilator.

The above objects are achieved in accordance with the principles of the present invention in an inspiratory tube of the initially-described type, having a constriction disposed in the gas flow channel between the distal end of the inspiratory tube and the opening adapted for connection to an expiratory device, a first channel proceeding within the wall generally parallel to the gas flow channel and opening into the gas flow channel at a location between the distal end of the inspiratory tube and the constriction, and a second channel proceeding within the wall generally parallel to the gas flow channel, and opening into the gas flow channel between the constriction and the opening adapted for connection to an expiratory device, with the first and second channels being adapted for connection to a pressure gauge for determining a rate of flow and pressure of gas flowing in the gas flow channel.

A number of advantages are achieved when the inspiratory valve is devised with a constriction in the gas flow channel, between one end of the inspiratory tube and an opening for an expiratory device, and channels that proceed inside the wall of the inspiratory tube and open into the gas flow channel at either side of the constriction. The pressure gauge/flow meter can be connected to the channels and measure pressure/flow between the expiratory valve and the distal end of the inspiratory tube, i.e. close to the patient. These measurements are a prerequisite for a control unit to calculate and regulate a flow of gas in such a way that the flow of gas maintains a PEEP for the patient when the tube is used with a ventilator.

Placing pressure/flow rate measurement functions near the patient also means that every attempt by the patient to inhale can be sensed in a simple and reliable manner. The patient can then be provided with rapid assistance for a new inspiration (inhalation). A flow of breathing gas is also already present at the expiratory valve. When this valve is closed, an inspiratory gas flow at a specific pressure and with a specific flow rate profile can be rapidly generated and supplied to the patient. This rapid response to attempted inspiration is not available with the aforementioned known inspiratory tube and ventilators.

The inspiratory tube can be devised with a dispensing channel arranged in its wall, generally parallel to the gas flow channel, and the dispensing channel is arranged with an opening into the gas flow channel between the distally spaced opening and the distal end of the inspiratory tube. The dispensing channel can also be connected to a dispensing unit for dispensing an additive gas into the gas flow channel.

In a corresponding manner, an additional channel, from which gas samples can be extracted, can be arranged in the wall of the inspiratory channel. This channel can appropriately open into the gas flow channel between the distally spaced opening and the distal end.

The constriction can appropriately be integrally formed as part of the inspiratory tube.

An expiratory control channel can also be arranged in the wall, generally parallel to the gas flow channel, and having an opening to ambient atmosphere between the distally spaced opening and the inspiratory tube's proximal end. The expiratory control channel can be connected to an expiratory valve and a source of compressed gas for controlling expiratory phases.

The different channels proceed appropriately through one or more reinforcements of the wall of the inspiratory tube.

These reinforcements can be devised so the cross-section of the inspiratory tube is unique and so the tube can only be connected to the ventilator in one way.

DESCRIPTION OF THE PREFERRED EMBODIMENTS

Figure 1:
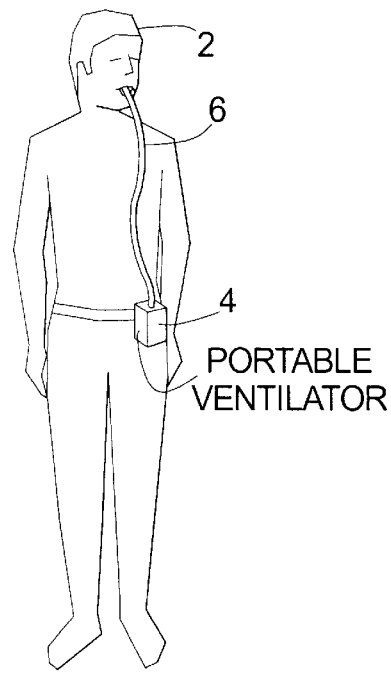
FIG. 1 shows the use of a fully portable ventilator according to the invention.

FIG. 1 shows how a patient 2 can become almost completely mobile with the aid of a fully portable ventilator 4. The patient 2 is connected to the ventilator 4 in some suitable fashion via an inspiratory tube 6. Connecting the fully portable ventilator 4 via a nasal route is preferable, since the patient 2 would then find it easier to speak and communicate with others. It should be noted that the fully portable ventilator 4 can also be connected in other ways, e.g. via a face mask, tracheal tube or tracheostomy/ tracheotomy tube. The latter implements are preferable when the ventilator 4 is used in emergencies or for patients 2 requiring greater breathing assistance.

Figure 3:
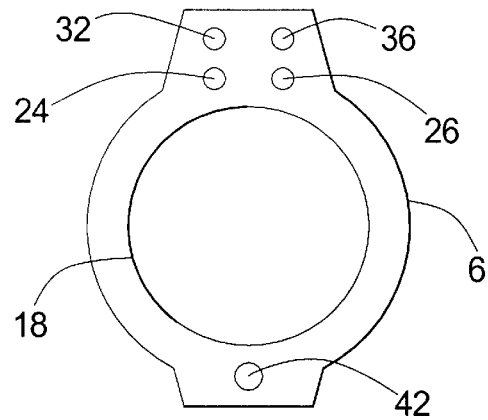
FIG. 3 shows a cross-section of the inspiratory tube of FIG. 2.
Figure 2:
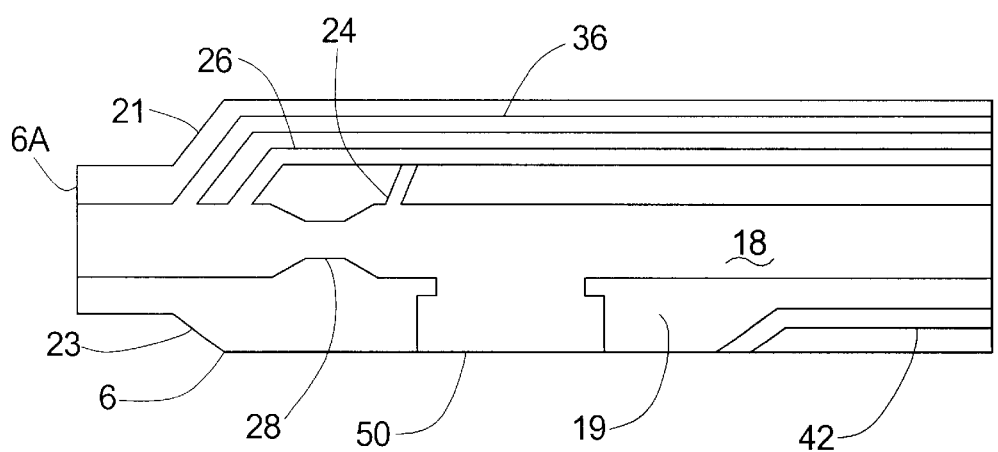
FIG. 2 shows a longitudinal section of an inspiratory tube in the ventilator according to the invention.

FIGS. 2 and 3 show details of the inspiratory tube 6. It should be noted that the inspiratory tube 6 can be formed as a complete inspiratory line or can be a part of an inspiratory line in a ventilator system. The design of the inspiratory tube 6 makes it particularly suitable for portable ventilator systems.

The inspiratory tube 6 according to the invention contains a gas flow channel 18 surrounded by a casing or wall 19. An opening 50 is arranged at a specific distance from the distal end 6A of the inspiratory tube 6. An expiratory device (described below) can be connected to this opening 50. A constriction 28 is arranged in the gas flow channel 18 between the opening 50 and the distal end 6A. The constriction 28 causes a drop in the pressure of gas as which flows across the constriction 28, the drop being proportional to the rate of flow. This accordingly makes it possible to measure both flow and pressure near the distal end 6A (to which a patient is attached when the inspiratory tube 6 is used) in a simple, space-saving fashion.

The wall 19 has reinforcements 21, 23 on the upper and lower sides of the inspiratory tube 6 to provide space for a number of channels. These reinforcements 21, 23 (and distribution of the channels around the gas flow channel 18) can naturally be devised in virtually any fashion but are advantageously asymmetrical or arranged in such a way that the cross-section of the inspiratory tube 6 is unique. This design then functions as a key-indexing to guarantee correct connection of the inspiratory tube 6 to a ventilator or some other device intended for the inspiratory tube 6.

Thus, a first channel 24 proceeds through the upper reinforcement 21. The first channel 24 opens into the gas flow channel 18 between the constriction 28 and the opening 50. The first channel 24 can be connected at the other end to a pressure gauge (see below). A second channel 26 proceeds parallel to the first channel 24 through the upper reinforcement 21. The second channel 26 opens into the gas flow channel 18 between the constriction 28 and the distal end 6A. The second channel 26 can also be connected at the other end to a pressure gauge (see below).

A gas sampling channel 32 and a dispensing channel 36, both of which open into the gas flow channel 18 between the constriction 28 and the distal end 6A, also proceed through the reinforcement 21 of the upper wall 19. An expiratory control channel 42 runs through the lower reinforcement of the wall 19. This channel opens into ambient atmosphere at a point proximal to the opening 50. The object of these channels 32, 36, 42 will be evident from the following.

Figure 4:
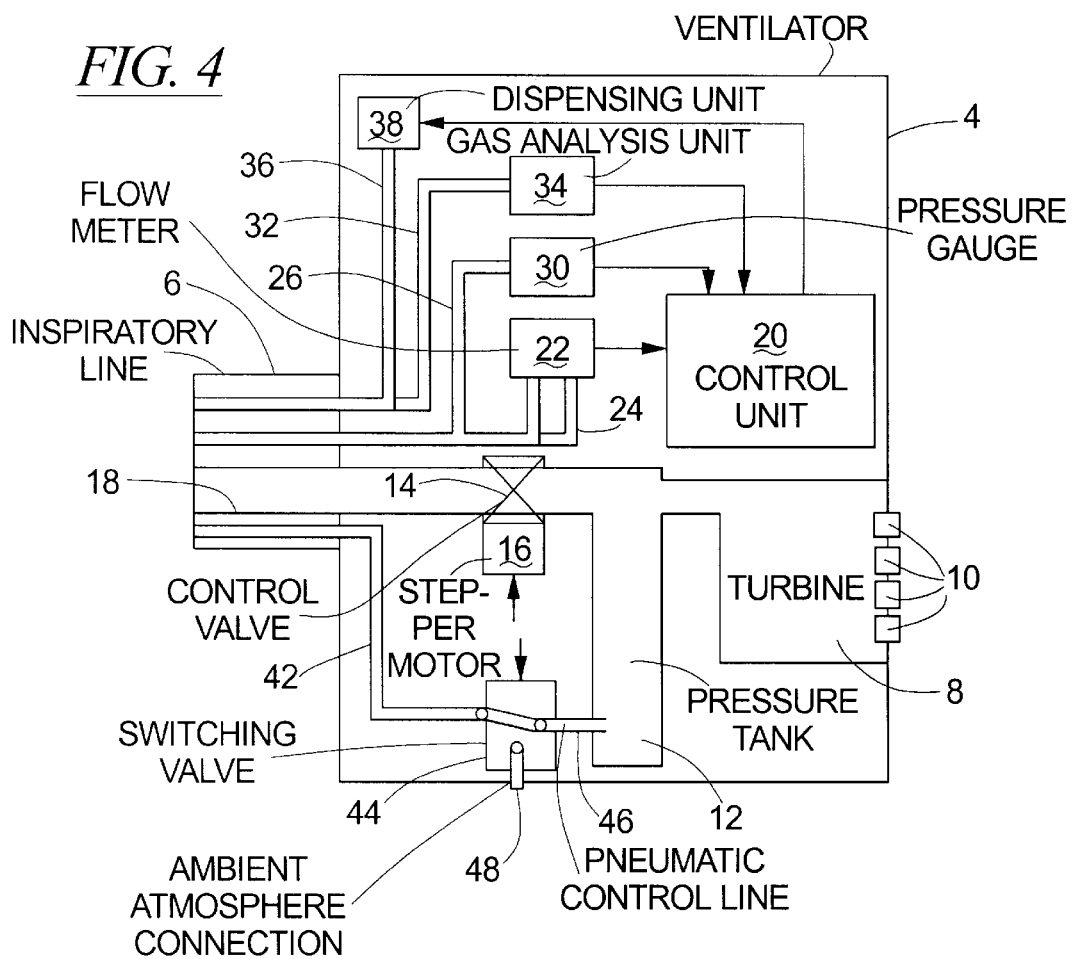
FIG. 4 shows the inspiratory tube according to the invention connected to a ventilator.
Figure 5:
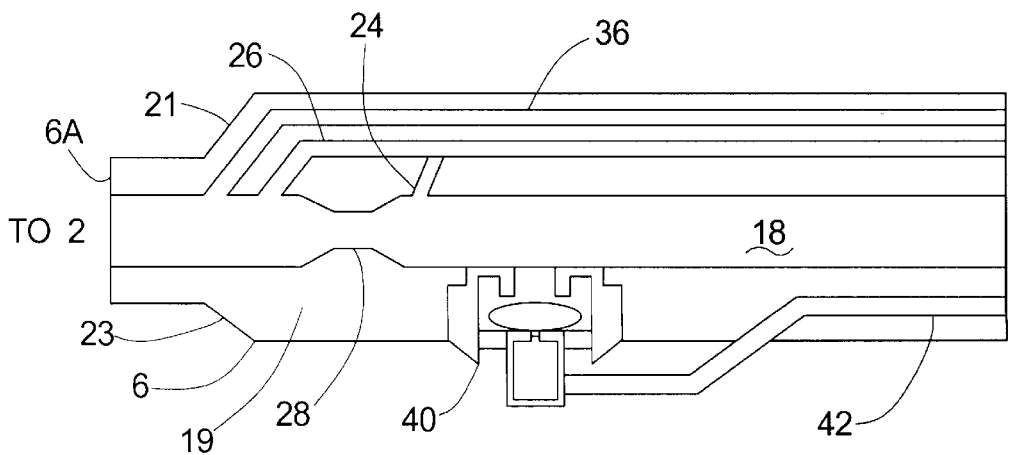
FIG. 5 shows the inspiratory tube according to FIG. 2 with an expiratory device connected thereto.

One embodiment of the ventilator 4, including the inspiratory tube 6, will now be described, referring simultaneously to FIGS. 4 and 6. Gas flow and pressure are generated by a turbine 8 connected to the atmosphere in some suitable fashion, e.g. via a number of openings 10 or the like. These openings 10 can also be equipped with filters to prevent any particles from being carried down into the lungs. The turbine 8 is connected to a pressure tank 12 holding breathing gas at a specific pressure generated by the turbine 8. The purpose of the pressure tank 12 is to make delivery to the patient 2 of breathing gas at a desired pressure and flow rate faster than if the turbine 8 were to generate pressure and flow from zero. The pressure tank 12 is relatively small, so it occupies less space and shortens the rise time for a pressure increase with a smaller volume. A control valve 14 is arranged after the pressure tank. In this instance, the control valve 14 is a 'scissors' valve regulated by a stepper motor 16. The control valve 14 regulates the flow of gas from the pressure tank 12 into a gas flow channel 18 in the inspiratory tube 6. The control valve 14 is also small, thereby enabling it to respond more rapidly to control signals (small inertia). This results, in turn, in the delivery of breathing gas, via the control valve 14, with steep gas pressure gradient. The gas flow channel 18 carries breathing gas to the patient 4 at the distal end 6A of the inspiratory tube 6.

The turbine 8, pressure tank 12, control valve 14 and stepper motor 16 jointly constitute a gas flow generator capable of generating an optional gas flow in the flow rate and pressure ranges relevant in the treatment of different kinds of patients. Although this construction of the gas flow generator is advantageous, especially in achieving fully portable ventilators 4, the gas flow generator can have other components. For example, a compressor or fan can replace the turbine 8. The turbine 8 can also be replaced with a pressurized source of gas, such as a gas cylinder or a piped compressed air system. The pressure tank 12 can be resilient or non-resilient or can be dispensed with completely. A resilient pressure tank can contribute to the generation of higher pressures by being compressible. In principle, the control valve 14 can be any kind of known valve. The stepper motor 16 can be dispensed with or replaced by some other known actuator, depending on the choice of the control valve 14. The components of the gas flow generator affect the size and portability of the ventilator 4. In principle, however, the same functionality can be achieved regardless of the components employed. The exact components used in the gas flow generator are not crucial to application of the invention.

The turbine 8 and the stepper motor 16 are controlled by a control unit 20. The control unit 20 can be formed by hardware, or by software or a combination thereof. The control unit 20 controls all functions in the ventilator 4 so parameter settings (made via a user interface, not shown) are maintained. The control unit 20 receives information on pressure and flow for use in maintaining those functions.

Flow information is received from a flow meter 22 which is connected to the distal end of the inspiratory tube 6 via a first channel 24 and a second channel 26. In principle, the channels 24, 26 proceed parallel to the gas flow channel 18 in the wall of the inspiratory tube 6 and open onto either side of a constriction 28 in the gas flow channel 18. The pressure of the gas drops when it flows through the constriction 28, the magnitude of the drop being related to the magnitude of the flow. Flow through the flow meter 22 therefore can be determined by measuring pressure on either side of the constriction 28. Since pressure is employed in this instance for determining the flow rate, the second channel 26 can be connected to a pressure gauge 30 in order to measure pressure at the distal end 6A of the inspiratory tube 6.

It should be noted that other flow meters, suitable for placement near the distal end 6A, can replace the flow meter 22. A separate channel would then be necessary for the pressure gauge 30. Since the flow meter 22 determines the flow rate from the pressure drop across the constriction 28, the pressure signal can be obtained straight from the flow meter 22 instead of from a separate pressure gauge 30.

A gas sampling channel 32, which terminates at the distal end 6A, extends through the inspiratory tube 6. Gas samples can be taken from the gas sampling channel 32 and analyzed in a gas analysis unit 34. The gas analysis unit 34 appropriately contains a pump for extracting the gas samples to be analyzed. Gas analysis can be performed to monitor carbon dioxide levels or check to ensure that sufficient breathing assistance is being provided. Gas analysis can also be performed to check on the composition of the breathing gas being supplied to the patient 2. If the gas and flow meters used are fast enough, carbon dioxide output and oxygen consumption can also be determined.

The latter is of interest when the inspiratory tube 6 contains a dispensing channel 36 for dispensing an additive gas to the patient 2. The dispensing channel 36 is connected to a dispensing unit 38 and opens into the gas flow channel 18 at the distal end 6A. The dispensing unit 38 includes a small gas cylinder containing additive gas and has a dispensing valve for regulating the amount dispensed. The additive gas can be oxygen or some other gas, such as NO. The dispensing unit 38 can also hold medication or some liquid additive which is dispensed through the dispensing channel 36 into the gas flow channel 18. The additive can be vaporized in this channel or dispersed in small droplets (atomized) before being delivered to the patient 2.

An expiratory valve 40 is also connected to the inspiratory tube 6. In the illustrated example, the expiratory valve 40 is built into the wall of the inspiratory tube 6 so it occupies as little space as possible. A tube or the like can also be connected between the inspiratory tube 6 and the expiratory valve 40 without affecting its function (as described below).

The expiratory valve 40 is connected to the gas flow channel 18 so that the constriction 28 and the openings of the channels 24, 26, 32, 36 lie between the expiratory valve 40 and the distal end 6A.

In this embodiment, the expiratory valve 40 is a pneumatically controlled ON/OFF valve (e.g. a mushroom valve). It is connected to the pressure tank 12 via a control channel 42 and a switching valve 44. The control channel 42 proceeds in the wall of the inspiratory tube 6, parallel to the gas flow channel 18 and other channels 24, 26, 32, 36. The switching valve 44 is controlled by the control unit 20.

During inspiratory phases (inhalation phases), the switching valve 44 is in a first position in which the control channel 42 is connected to the pressure tank 12 via a first gas connection 46. The expiratory valve 44 is then closed with the same actuating pressure (usually higher than the pressure of the breathing gas delivered to the patient 4) as the pressure in the pressure tank 12.

During expiratory phases, the switching valve 44 is switched to a second position in which the expiratory valve 40 is connected to the atmosphere via the control channel 42, the switching valve 44 and a second gas connection 48.

If a positive end-expiratory pressure (PEEP) is to be maintained for the patient 2, the control valve 14 is regulated so that a flow of gas is released through the gas flow channel 18 toward the patient 2, even during expiration. This flow of gas is controlled by the control unit 20 according to the pressure and flow measured between the expiratory valve 40 and the distal end 6A. This regulated flow of gas also flows out through the expiratory valve 40 but simultaneously serves as resistance in relation to the patient 4, who accordingly exhales against a pressure corresponding to the selected PEEP.

This kind of PEEP regulation was not previously possible, especially not in portable ventilators. Here, the placement of pressure/flow measurement between the expiratory valve 40 and the distal end 6A (the patient 4) plays a decisive role. PEEP cannot be regulated and maintained in this way unless information is available on pressure/flow at the patient 2.

This location for pressure/flow measurement also produces other advantages. For example, the ventilator 4 can be made to respond more rapidly to any efforts by the patient 2 to inhale (i.e. triggering). The ventilator 4 can in particular respond immediately to any inspiration commenced during expiration. Flow will then be registered as moving towards the patient 2, and the control unit 20 can respond immediately, closing the expiratory valve 40 and introducing an inspiratory flow of gas. This flow commences relatively quickly, since a flow of gas is already being maintained through the gas flow channel 18.

The placement of just about all the components in a common enclosure, with all the necessary gas channels arranged in the inspiratory tube 6, makes the ventilator 4 very compact and easy to use. The few parts (the enclosure and inspiratory tube 6) are interconnected in a suitable fashion. For example, known types of bayonet or pin (keyed) index connectors can be used. No additional cords or tubing, which could become entangled with each other or other objects, are needed. As noted above, the described embodiment is one advantageous version of a fully portable ventilator, but the embodiment can be utilized for a number of different applications. For example, it can be used as a home care ventilator for patients who do not require constant monitoring. It can also be used in ambulances or as an emergency ventilator. A third option is to use it for non-acute (non-critical care) treatment in hospitals. In other words, it can be employed for virtually every application for which a ventilator is needed. In all of these options, ventilator use is facilitated by the design of the inspiratory tube 6.

The portable ventilator is battery-powered. The batteries can naturally be rechargeable, and the provision of a parallel AC power source is a an option.

The ventilator does not need to incorporate every option. The ventilator 4 can be devised in both simpler and more complex versions. In principle, a simple version includes the turbine 8, pressure tank 12, control valve 14, stepper motor 16, control unit 20, flow meter 22 (doubling as a pressure gauge), inspiratory tube 6 (with the channels 18, 24, 26 and 42), expiratory valve 40, switching valve 44 and batteries (not shown). This kind of simple version of the ventilator 4, utilizing existing components, can be manufactured in about the same size as a portable cassette or CD player, i.e. about 10×10×2 cm and weigh a few hundred grams.

Although modifications and changes may be suggested by those skilled in the art, it is the intention of the inventor to embody within the patent warranted hereon all changes and modifications as reasonably and properly come within the scope of his contribution to the art.

I claim as my invention:

1. A breathing tube for use in a breathing-assist system, said tracheal tube comprising:

a tube wall having an interior surface and an exterior surface, said interior surface defining a gas flow channel with a distal end and a proximal end for carrying a flow of breathing gas therein;

said tube wall having an opening therein, proceeding through said tube wall from said interior surface to said exterior surface, at a distance from said distal end;

an expiratory valve disposed in said opening and communicating with ambient air;

said gas flow channel having a constriction therein between said distal end and said opening;

a first channel proceeding within said tube wall substantially parallel to said gas flow channel and opening into said gas flow channel between said distal end and said constriction;

a second channel proceeding within said tube wall substantially parallel to said gas flow channel and opening into said gas flow channel between said constriction and said opening; and said first and second channels being adapted for connection to a pressure gauge for determining at least one of flow and pressure of said breathing gas.

2. A breathing tube as claimed in claim 1 further comprising a dispensing channel disposed within said tube wall proceeding substantially parallel to said gas flow channel, said dispensing channel opening into said gas flow channel between said opening and said distal end, said dispensing channel being adapted for connection to a dispensing unit which dispenses an additive gas into said gas flow channel.

3. A breathing tube as claimed in claim 1 further comprising a gas sampling channel disposed within said tube wall and proceeding substantially parallel to said gas flow channel, said gas sampling channel opening into said gas flow channel between said opening and said distal end, said gas sampling channel being adapted for connection to a gas analyzer for analyzing gas in said gas flow channel.

4. A breathing tube as claimed in claim 1 further comprising an expiratory control channel disposed within said tube wall and proceeding substantially parallel to said gas flow channel, said expiratory control channel opening into ambient atmosphere between said opening and said proximal end, and said expiratory control channel being adapted for connection to an expiratory valve and to a source of compressed gas for controlling expiratory phases.

5. A breathing tube as claimed in claim 1 wherein said constriction comprises an integrally formed portion of said tube wall.

6. A breathing tube as claimed in claim 1 further comprising at least one reinforcement proceeding along an exterior of said tube wall, with at least one of said first and second channels being disposed in said reinforcement.

7. A breathing tube as claimed in claim 6 wherein said inspiratory tube, with said at least one reinforcement, has an asymmetrical cross-section in a plane substantially perpendicular to said gas flow channel.

* * * * *